(12) United States Patent
Klovning

(10) Patent No.: US 6,923,038 B2
(45) Date of Patent: Aug. 2, 2005

(54) DEVICE FOR MEASURING OF FRICTION

(75) Inventor: Bjarne Klovning, Hareid (NO)

(73) Assignee: FM Equipment AS (NO)

( * ) Notice: Subject to any disclaimer, the term of this patent is extended or adjusted under 35 U.S.C. 154(b) by 151 days.

(21) Appl. No.: 10/221,361

(22) PCT Filed: Mar. 13, 2001

(86) PCT No.: PCT/NO01/00108
§ 371 (c)(1),
(2), (4) Date: Jan. 14, 2003

(87) PCT Pub. No.: WO01/71315
PCT Pub. Date: Sep. 27, 2001

(65) Prior Publication Data
US 2003/0159494 A1 Aug. 28, 2003

(30) Foreign Application Priority Data
Mar. 13, 2000 (NO) .......................................... 2000 1294

(51) Int. Cl.$^7$ ............................................. G01N 19/02
(52) U.S. Cl. ............................................................. 73/9
(58) Field of Search ......................................... 73/9, 10

(56) References Cited

U.S. PATENT DOCUMENTS

| | | | | |
|---|---|---|---|---|
| 2,700,297 A | * | 1/1955 | Allen ............................... | 73/9 |
| 4,467,661 A | * | 8/1984 | Somal .................... | 73/862.382 |
| 4,662,211 A | | 5/1987 | Strong | |
| 5,705,746 A | | 1/1998 | Trost et al. | |
| 6,192,736 B1 | * | 2/2001 | Clem ............................... | 73/9 |
| 6,463,784 B2 | * | 10/2002 | Kashiwagi et al. .............. | 73/9 |

FOREIGN PATENT DOCUMENTS

EP    0748730 A1    12/1996

* cited by examiner

Primary Examiner—Robert Raevis
(74) Attorney, Agent, or Firm—Nixon & Vanderhye PC

(57) ABSTRACT

The present invention concerns a device to be mounted on a vehicle that is in a position to measure, by means of own equipment, different data which is important for the road safety on roads and runways for aircrafts. The device is among other factors equipped with a measuring cell from which it is possible to directly read the pressure that exerts against the wheel when it impinges on the roadway. It is further possible to read the velocity of the wheel, and the acceleration/retardation.

12 Claims, 2 Drawing Sheets

DEVICE FOR MEASURING OF FRICTION

Figure 1:
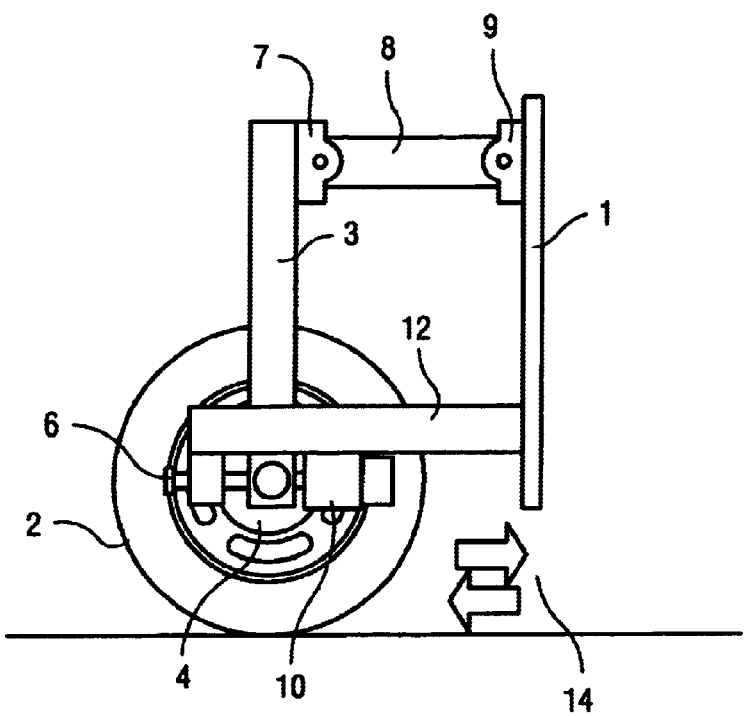

This application is the US national phase of international application PCT/NO01/00108 filed 13 Mar. 2001, which designated the US.

The present invention relates a device for measuring inter alia of the resistance and/or friction between the wheel of a vehicle and the roadway, or between the landing gear and the runway of an aircraft when it is moving on the ground.

As the conditions have developed the requirements regarding traffic safety have increased. An essential factor in this connection is the friction that has to be present between wheel and roadway.

This concerns all types of wheels of vehicles, which are moving on a roadway.

It is, however, not satisfactory to know that friction is present, but you ought to know that the friction is large enough.

To estimate if the friction is large enough, you ought to have units of measurement and they have to be comparable. The units of measurement must have references.

Until now the concept regarding friction measuring has not been adequate, as there has not been equipment that has been in a position to estimate this in a way that could have given references of lasting character.

Before one is in a position to obtain this, one ought to have friction measuring units that can be referenced to and are comparable with others.

This also applies to runways on airports to be used by aircrafts.

Frequently one may observe that pilots disagree with the ground personnel regarding frictions activity e.g. on the landing strip. This is mainly often a result of disagreement regarding the basis values the measures refer to, and to the inequality between the equipment that is used for the measurement.

The reason for this is due to lack of measuring equipment that is capable of giving fixed values with accessible references.

This is due to friction that arises during braking has a very complex course which is influenced by many factors inter alia the surface of the ground, the velocity of the vehicle, air temperature, the design of the tyres, the rubber quality of the tyres and at least if it is snow or ice on the ground. Above all the factor that until now has shown to be of greater significance, namely if the runway is covered by water, the size of the water area, and what kind of properties the water has. As an example it can be mentioned that water whipped with air has totally different properties than water which is not mixed with air.

It is this last condition that one has not been aware of and taken it into account.

It is therefore to comply with the requirement for a device for measuring of friction and resistance that the present invention may be of help in a way that the reading can have the same international basis values. Those who receive the figure values will be certain that the reading do not deviate, or has other references than some other under the same conditions.

First when this situation has been solved, we have a complete measuring system and achieve a better traffic safety in this sector.

To obtain a satisfactory system one has to divide the individual affecting factors, although they may have minor significance on the result, but the most important is that one knows the main factors and concentrates on the one with greatest significance.

The object of the invention is to provide a device that is capable of recording data in an easy and safe way. The data must be converted and displayed on a monitor for instance in the drivers cabin of a vehicle. In this way it is possible to read the correct values and they will give the actual friction conditions and the resistance on the carriage way.

There is a great difference in the way the water affects on the friction measuring devices. Water falling for instance as rain during sampling, is quite different from water laying still on the road, and if the added water for simulation is rainwater.

Likewise the quantity of water (the depth) is of great importance regarding resistance. During generation of the present invention, is it possible to eliminate a number of the usual occurring factors, in a way that you may read the values directly on a monitor without converting external data regarding the condition of the road, tyres, water density and so on.

The device according to the present invention comprises mainly of a rubber wheel with a ABS braking system. The wheel is secured to a bracket which in an easy way can be fastened to a vehicle which is equipped to carry out tests.

The bracket is again screw fastened to the front of the vehicle, and the wheel can be placed down to the roadway with a suitable pressure. The wheel is suspended in a link which may pivot limited in the vertical plane, and in that way absorb minor unevennesses on the roadway.

The wheel will receive the exposed pressure when it is moving in front of the vehicle. Counter pressure and pressure will in other words be equal. The pressure the wheel withstands is an important factor to provide the data.

The pressure will all along vary depending on the external condition. It is important for the sampling to exactly know the pressure. To estimate the pressure and the variation and so on, a measuring cell with great accuracy absorbs the pressure and via electronic equipment can display the same on a data monitor in the cabin of the vehicle.

U.S. Pat. No. 4,958,512 describes a device for measuring of brake forces. A vertical and a horizontal force are applied to a rolling wheel. The brake force is changing continuously to find the optimum friction values. The device is mounted on a pulling vehicle.

U.S. Pat. No. 4,098,111 discloses a system and apparatus for using a raisable and lowerable wheel with a device for detecting of vertical and horizontal loads. The apparatus has a relative complex configuration and is mounted in the rear of an automobile.

The invention will now be described with references to the drawings wherein the reference numbers to the components corresponds to the numbers in the description.

Figure 2:
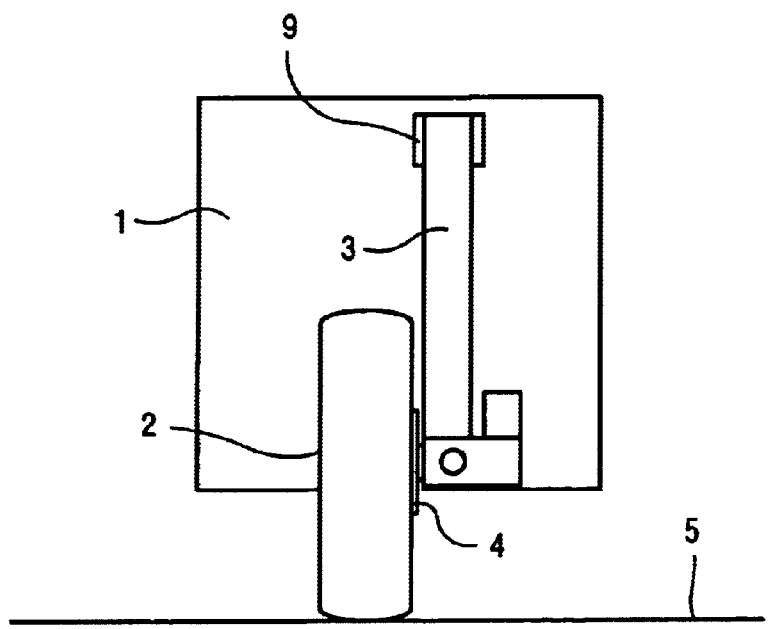
Figure 3:
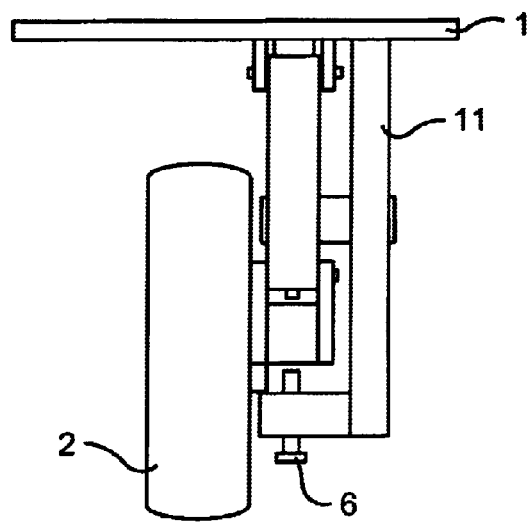
Figure 4:
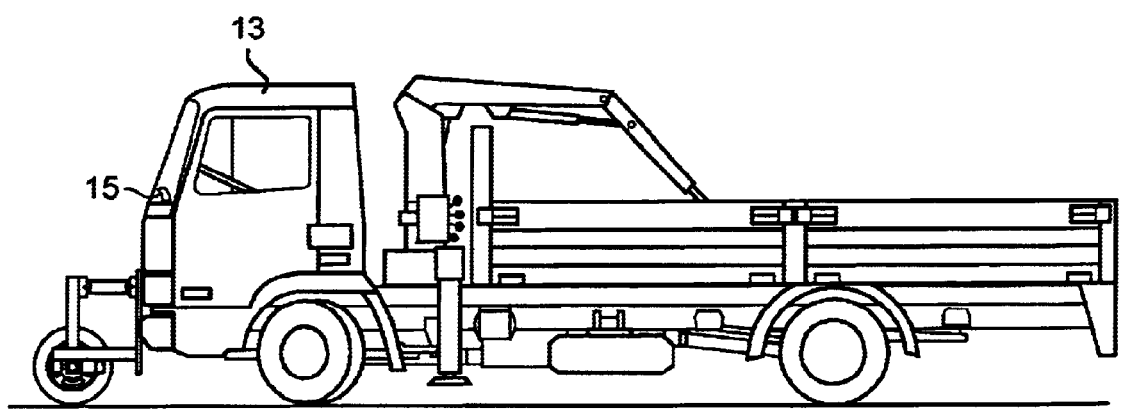

FIG. 1 shows the device according to the invention with wheel seen form the side, FIG. 2 shows the device seen from ahead, FIG. 3 shows the device seen from above, FIG. 4 shows the device mounted in front of a vehicle.

FIG. 1 seen from the side and FIG. 2 seen from ahead, shows a bracket 1 or a fastening plate that on one side the device is secured to, and the other side is secured to a vehicle. The vehicle 13 in FIG. 4 wherein the device is depicted, is located in front of the vehicle.

The device further comprises at least one rubber wheel 2 that preferably by means of its own weight impinges the ground 5. In the wheel is a nave 4 equipped with brakes preferably of ABS type.

The suspension of the wheel comprises a vertical holder 3 that is supported in the upper edge and may pivot around this point 7 as a pendulum. The arm 8 is also movable around its supporting locality 9 that has its attachment in the plate 1 which is secured to the vehicle 13.

To avoid that the vertical holder is getting out of its precise position during driving, it is equipped with an adjusting screw 6 located on a pendant arm 11 which provides that it does not fit too loose. The vertical holder may in a certain degree move and down, and will all the time be in touch with the roadway with a pressure. The wheel may also be provided with a spring that keeps the wheel towards the roadway with a constant pressure. This is not shown in the figures.

When the vehicle is moving forward as depicted in the figure there will arise a pressure from the wheel 2 toward the vehicle, and this is shown with an arrow 14. A measuring cell 10, which is installed on the permanent pendant girder 12 from the bracket 1 receives this pressure.

From the measuring cell there is a connecting line to the computer inside the driver's cab, which displays the pressure on a monitor display 15. Before the pressure is shown on the display, it is calibrated in proportion to the weight arm, which is situated between the centre of the wheel and the point of attack to the measuring cell.

To obtain the data, the test vehicle drives on the roadway, and it is possible to read on the display the correct velocity in units of length per unit time e.g. km/h or hm/h.

It is further possible to read the acceleration directly in m/s/s or the retardation in the same units.

An important aspect is that the device according to the invention is located in front of the vehicle.

By setting a velocity, it is possible to read directly on the display the resistance that exists in different velocities.

One has to choose a basis of units and implement the deviation, which occurs when the roadway is wet, when it is much water on the ground and so on.

By reading the display of the measuring cell it is possible to establish the resistance of the water.

By utilise the brake of the wheel it is possible to evaluate the braking effect, how large the resistance is during different roadway conditions and so on.

The obtained data can be coordinated and converted to units that can be compared from time to time. After some tests it is possible to get exactly the units of measure you are in need of.

These can be processed further and preferably be brought to international approval and use.

What is claimed is:

1. Assembly for measuring forces on road surfaces and runways comprising:

a vertical holder connected to a front of a power driven vehicle;

at least one wheel supported on said vertical holder;

a first horizontal arm connected to said front of said vehicle;

a measuring cell mounted to said first horizontal arm and disposed adjacent at least one of said vertical holder and/or said wheel, said measuring cell being at least selectively operatively coupled to at least one of said vertical holder and/or said wheel to detect net forces acting on said wheel in a direction toward said vehicle when said vehicle is moving forward.

2. Assembly according to claim 1, further comprising a limit stop structure for limiting movement of at least one of said wheel and said vertical support in a direction away from said front of said vehicle.

3. Assembly according to claim 2, wherein said limit stop comprises an adjusting screw disposed substantially diametrically opposite said measuring cell.

4. Assembly according to claim 3, further comprising a second horizontal arm extending from said front of said vehicle and having said limit stop structure mounted thereto.

5. Assembly according to claim 1, wherein said vertical holder is connected to said front of said vehicle via a mounting plate.

6. Assembly according to claim 5, wherein said first horizontal arm extends forwardly from said mounting plate.

7. Assembly according to claim 1, wherein said vertical holder is connected to said front of said vehicle with a connecting structure comprising a support arm extending forwardly from said front of said vehicle.

8. Assembly according to claim 7, wherein said vertical holder is pivotally coupled to said arm support.

9. Assembly according to claim 8, wherein said arm is pivotally connected to a mounting plate mounted to said front of said vehicle.

10. Assembly according to claim 1, wherein the measuring cell is connected to a monitor for indicating net horizontal forces on said wheel as measured.

11. Assembly according to claim 1, wherein the wheel has installed brakes.

12. Assembly according to claim 11, wherein said brakes are ABS brakes.

* * * * *